(12) United States Patent
Tran et al.

(10) Patent No.: US 10,954,280 B2
(45) Date of Patent: Mar. 23, 2021

(54) METHOD OF PURIFICATION OF RECOMBINANT OSTEOPONTIN FROM MICRO ALGAE

(71) Applicant: Triton Algae Innovations, Inc., San Diego, CA (US)

(72) Inventors: Miller Tran, San Diego, CA (US); Michael Mayfield, San Diego, CA (US); Jeremy Ferrara, San Diego, CA (US)

(73) Assignee: Triton Algae Innovations, Inc., San Diego, CA (US)

(*) Notice: Subject to any disclaimer, the term of this patent is extended or adjusted under 35 U.S.C. 154(b) by 0 days.

(21) Appl. No.: 16/349,116

(22) PCT Filed: Nov. 16, 2017

(86) PCT No.: PCT/US2017/061916
§ 371 (c)(1),
(2) Date: May 10, 2019

(87) PCT Pub. No.: WO2018/098001
PCT Pub. Date: May 31, 2018

(65) Prior Publication Data
US 2019/0276508 A1    Sep. 12, 2019

Related U.S. Application Data (60) Provisional application No. 62/426,567, filed on Nov. 27, 2016.

(51) Int. Cl.
| | |
|---|---|
| *C07K 14/47* | (2006.01) |
| *C12N 1/12* | (2006.01) |
| *C12N 15/82* | (2006.01) |
| *C12R 1/89* | (2006.01) |

(52) U.S. Cl.
CPC ............ *C07K 14/473* (2013.01); *C07K 14/47* (2013.01); *C12N 1/12* (2013.01); *C12N 15/8257* (2013.01); *C12R 1/89* (2013.01)

(58) Field of Classification Search
None
See application file for complete search history.

(56) References Cited

U.S. PATENT DOCUMENTS

| | | |
|---|---|---|
| 8,969,066 B2 | 3/2015 | Mendez et al. |
| 2003/0149249 A1 | 8/2003 | Sorensen et al. |
| 2004/0014174 A1 | 1/2004 | Mayfield et al. |
| 2007/0134229 A1 | 6/2007 | Tian |
| 2009/0325240 A1 | 12/2009 | Daniell |
| 2011/0189228 A1 | 8/2011 | Bayne et al. |
| 2015/0284673 A1 | 10/2015 | Langer et al. |
| 2016/0257730 A1 | 9/2016 | Mayfield et al. |

FOREIGN PATENT DOCUMENTS

| | | |
|---|---|---|
| WO | 1994002625 A1 | 2/1994 |
| WO | 2009027284 A1 | 3/2009 |
| WO | 20110384863 A1 | 3/2011 |
| WO | 2011063284 A1 | 5/2011 |
| WO | 2015126992 A1 | 8/2015 |

OTHER PUBLICATIONS

Rhodes, D.G. & Laue, T.M., (2009) 'Chapter Thirty-Eight: Determination of Protein Purity' in Methods of Enzymology, vol. 263, pp. 677-689. DOI: 10.1016/50076-6879(09)63038-X.*

Yuan et al., "Expression and Purification of Bioactive High-Purity Recombinant Mouse SPP1 in *Escherichia coli*", Appl Biochem Biotechnol (2014) 173:421-432. DOI 10.1007/s12010-014-0849-7.*

PCT/US2017/061916 ISR and WO dated Feb. 21, 2018.

* cited by examiner

*Primary Examiner* — Suzanne M Noakes
(74) *Attorney, Agent, or Firm* — Wagenknecht IP Law Group, PC (57) ABSTRACT

Provided herein are methods for obtaining purified recombinant osteopontin (rOPN) from cultures of transgenic microalgae, as well as nutritional supplements from such cultures.

18 Claims, 3 Drawing Sheets
Specification includes a Sequence Listing.

METHOD OF PURIFICATION OF RECOMBINANT OSTEOPONTIN FROM MICRO ALGAE

CROSS REFERENCE TO RELATED APPLICATION(S)

This application is a US national phase application under 35 U.S.C. § 371 of international patent application no. PCT/US2017/061916, filed Nov. 16, 2017, which claims the benefit of priority under 35 U.S.C. § 119(e) of U.S. Ser. No. 62/426,567, filed Nov. 27, 2016, the entire content of each of which is incorporated herein by reference.

SEQUENCE LISTING

The instant application contains a Sequence Listing which has been submitted electronically in ASCII format and is hereby incorporated by reference in its entirety. Said ASCII copy, created on Dec. 29, 2017, is named "20498-201678_SL.txt" and is 2 Kilobytes in size.

BACKGROUND

Osteopontin (OPN) is an acidic multifunctional protein of approximately 300 amino acids that was first identified in 1979. Osteopontin exists in several isoforms due to extensive post-translational modification. Characterization of post-translational modifications has been conducted for OPN obtained from several species and sources. Bovine milk OPN has 28 phosphorylation sites as well as 3 sites for O-glycosylation. The slightly larger human milk OPN contains 38 phosphorylation sites and 5 O-glycosylation sites, while human urinary OPN also has 5 O-glycosylation sites, but only 31 phosphorylation sites. Rat bone OPN possesses at least 29 phosphorylation sites, 4 O-glycosylation sites and a site of tyrosine sulfation. Osteopontin secreted by mouse osteoblast cultures has 27 phosphorylation and 5 O-glycosylation sites. In addition to the number of phosphorylation sites, the extent of phosphorylation varies between isoforms. For example, although all 28 phosphorylation sites are fully modified in cow's milk OPN, only about 8 of the 31 phosphorylation sites are modified in human urinary OPN. In addition, OPN contains an RGD (arginine, glycine, aspartate) integrin-binding sequence which promotes attachment of cells to various surfaces.

Since its discovery, OPN has been implicated in many biological functions including, activation of cell-mediated immune responses, inhibition of calcification, and neonatal immune development. In human breast milk, OPN has been shown to be crucial for infant immunity. Osteopontin stimulates T-cells to differentiate into T-helper 1 (Th-1) cells by inducing T-cells to secrete IL-12. Th-1 cells are known to be crucial for assisting macrophages by enhancing phagocytosis of bacteria or protozoa, improving viral clearance and maximizing the proliferation of CD8 T-cells. In contrast, OPN down regulates the secretion of IL-10 and limits the production of T-helper 2 (Th-2) cells. Osteopontin also has an opsonizing effect, binding to pathogens and marking them for phagocytosis. These factors indicate an important role for OPN in neonatal and infant gut development.

Osteopontin's role in infant immunity is well known. Previous studies have demonstrated the disparity between the concentration of OPN in cow's milk and human breast milk. In some studies OPN has been shown to account for 10% of human breast milk. This disparity is further highlighted when the concentration of OPN in human milk is compared to that found in infant formula, which is primarily derived from bovine milk. Thus, the ability of infant formula to mimic the nutritional value of breast milk could be improved by the addition of OPN. At present, the only source of OPN on a commercial scale is cow's milk. The use of cow's milk to supplement infant formula, however, is not considered commercially feasible due to the combination of low levels of OPN in cow's milk and the high cost of purification. Previous attempts to develop alternative sources of OPN, such as OPN produced in *E. coli* have resulted in production of a protein that was biologically inactive due to a lack of phosphorylation.

Over the past 40 years, recombinant protein expression systems have been developed to meet the growing demand for proteins. These systems, however, are often expensive and are therefore reserved for producing high value proteins used in therapeutics. The idea of using a recombinant protein expression system for the production of proteins with nutritional value is rarely considered, mainly because of the underlying cost especially those associated with extensive protein purification. Over the past 10 years there has been significant interest and considerable investment in the large scale and affordable production of green algae for use in biofuels. The advances made in algae genetics, growth, and productivity for biofuels can now be harnessed for the production of recombinant proteins.

*Chlamydomonas reinhardtii* is a eukaryotic green algae that has been developed as a recombinant protein expression system over many years. The nuclear, chloroplast, and mitochondrial genomes of *C. reinhardtii* have been sequenced and transformed. Specifically, the chloroplast of *C. reinhardtii* has been turned into a robust expression system through the development of advance protein expression cassettes and an increased understanding of the biology of this organelle. Recently, chloroplasts of green alga have been used to express phosphorylated, bioactive OPN (US Patent Application Publication 2016/0257730). With the ability to produce recombinant OPN on a commercial scale, the need arises for an economically feasible method that will allow purification of OPN produced from micro algae. The current disclosure provides such a method.

SUMMARY

Provided herein is a method for obtaining a purified recombinant osteopontin (rOPN) expressed by a transgenic microalgae by disrupting the cell structure of the microalgae in a liquid environment. In certain embodiments, the microalgae cell structure is disrupted by at least one method selected from freezing and thawing, bead beating, acid hydrolysis, homogenization, microfluidization, use of a French press, sonication, enzymatic treatment, or nitrogen decompression. In one embodiment the liquid environment has a first pH of between about pH 4.3 and about pH 8.5, while in another embodiment the first pH of the liquid environment is between about pH 4.3 and about 6.0. In a particular embodiment, the first pH of the liquid environment is about pH 5.0.

Disruption of the microalgae cell structure results in the formation of soluble and insoluble cell fractions, with the soluble cell fraction containing the rOPN. The soluble and insoluble cell fractions are separated by any means known in the art, for example, centrifugation, filtration, sedimentation or a combination of these methods. In certain embodiments the soluble and insoluble cells fractions are separated by centrifugation at 10,000×g. The pH of the soluble fraction is adjusted to a second pH of between about pH 5.0 and about pH 9.0 in the presence of a soluble calcium salt to form a precipitate containing the rOPN and a supernatant. In certain embodiments, the pH is adjusted to a second pH between about pH 6.0 and about pH 8.5 or between about pH 7.0 and about pH 8.5. In still further embodiments the soluble fraction is adjusted to a second pH of about pH 8.0. In additional embodiments, the soluble calcium salt may be calcium chloride, calcium citrate, calcium sulphate, calcium fluoride, calcium phosphate or calcium carbonate. In a particular embodiment, the soluble calcium salt is calcium chloride at a concentration of between about 100 mM and about 250 mM. In some embodiments, the precipitate containing the rOPN and the supernatant are separated by centrifugation, sedimentation and/or filtration. In one embodiment, the precipitate and supernatant are separated by centrifugation at 10,000×g.

The rOPN within the precipitate is solubilized by adjusting the pH to a third pH between about pH 4.3 and about pH 5.0. In some embodiments, the third pH is between about pH 4.5 and 5.0 or between about pH 4.7 and about pH 5.0. In a particular embodiment the third pH is about pH 5.0. Following increasing the pH to the third pH, the calcium salt is removed by sedimentation, centrifugation and/or filtration. In one embodiment, the calcium salt is removed by centrifugation at 10,000×g. The solubilized rOPN is then bound to an anion exchange medium which may be a weak or strong anion exchange medium. In some embodiments DEAE-sepharose is utilized as a weak anion exchange medium and a Q-resin is used as a strong anion exchange medium. The bound rOPN is then eluted from the anion exchange medium. In some embodiments the bound rOPN is eluted from the anion exchange medium with a competing salt. In one embodiment the completing salt is sodium chloride. In a particular embodiment, the bound rOPN is eluted using sodium chloride at a concentration between about 200 mM and about 400 mM. The rOPN is collected as it is eluted from the anion exchange medium to yield a purified rOPN. The degree of purification can range from greater than 20% pure to greater than 99% pure.

BRIEF DESCRIPTION OF THE DRAWINGS

FIG. 3 shows expression of bovine OPN in algae (FIG. 3A) and that the strain is homoplasmic (FIG. 3B).

DETAILED DESCRIPTION

The following detailed description is provided to aid those skilled in the art in practicing the claimed invention. This detailed description should not, however, be construed to unduly limit the claimed invention as modifications and variations in the embodiments discussed herein can be made by those of ordinary skill in the art without departing from the scope of the presently claimed inventive discovery.

All publications, patents, patent applications, public databases, public database entries, and other references cited in this application are herein incorporated by reference in their entirety as if each individual publication, patent, patent application, public database, public database entry, or other reference was specifically and individually indicated to be incorporated by reference.

As used in this specification and the appended claims, the singular forms "a", "an" and "the" include plural reference unless the context clearly dictates otherwise.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed. The upper and lower limits of these smaller ranges can independently be included or excluded in the range, and each range where either, neither or both limits are included in the smaller ranges is also encompassed, subject to any specifically excluded limit in the stated range. Where the stated range includes one or both of the limits, ranges excluding either or both of those included limits are also included.

Provided herein are methods for the production of purified preparations of recombinant osteopontin (rOPN) obtained from genetically transformed microalgae. A "microalgae", as used herein, is a non-vascular alga and may include organisms classified as photosynthetic bacteria (including cyanobacteria). It should be noted that in the present disclosure the terms microalgae and algae are used interchangeably.

Non-limiting examples of genera of microalgae that may be used to produce rOPN include Cyanophyta, Prochlorophyta, Rhodophyta, Chlorophyta, Heterokontophyta, Tribophyta, Glaucophyta, Chlorarachniophytes, Euglenophyta, Euglenoids, Haptophyta, Chrysophyta, Cryptophyta, Cryptomonads, Dinophyta, Dinoflagellata, Pyrmnesiophyta, Bacillariophyta, Xanthophyta, Eustigmatophyta, Raphidophyta, Phaeophyta, and Phytoplankton. A microalgae may also be a microalgae species including, but not limited to, *Chlamydomonas reinhardtii, Dunaliella salina, Nannochloropsis salina, Nannochloropsis occulata, Scenedesmis dimorphus, Scenedesmus obliquus, Dunaliella tertiolecta*, or *Haematococcus pluvialis*. A "microalgae" of the present disclosure may be a unicellular non-vascular organism. In other instances, the microalgae may be one or more cells of a multicellular non-vascular organism.

Additional non-limiting examples of microalgae species that can be used with the methods of the present disclosure include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tennis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella Candida, Chlorella capsulate, Chlorella desiccate, Chlorella ellipsoidea, Chlorella emersonii, Chlorella fusca, Chlorella fusca* var. *vacuolate, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella* regularis var. minima, Chlorella regularis var. umbricata, Chlorella reisiglii, Chlorella saccharophila, Chlorella saccharophila var. ellipsoidea, Chlorella salina, Chlorella simplex, Chlorella sorokiniana, Chlorella sp., Chlorella sphaerica, Chlorella stigmatophora, Chlorella vanniellii, Chlorella vulgaris, Chlorella vulgaris fo. tertia, Chlorella vulgaris var. autotrophica, Chlorella vulgaris var. viridis, Chlorella vulgaris var. vulgaris, Chlorella vulgaris var. vulgaris fo. tertia, Chlorella vulgaris var. vulgaris fo. viridis, Chlorella xanthella, Chlorella zofingiensis, Chlorella trebouxioides, Chlorella vulgaris, Chlorococcum infusionum, Chlorococcum sp., Chlorogonium, Chroomonas sp., Chrysosphaera sp., Cricosphaera sp., Crypthecodinium cohnii, Cryptomonas sp., Cyclotella cryptica, Cyclotella meneghiniana, Cyclotella sp., Dunaliella sp., Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera sp., Ellipsoidon sp., Euglena spp., Franceia sp., Fragilaria crotonensis, Fragilaria sp., Gleocapsa sp., Gloeothamnion sp., Haematococcus pluvialis, Hymenomonas sp., Isochrysis aff galbana, Isochrysis galbana, Lepocinclis, Micractinium, Micractinium, Monoraphidium minutum, Monoraphidium sp., Nannochloris sp., Nannochloropsis salina, Nannochloropsis sp., Navicula acceptata, Navicula biskanterae, Navicula pseudotenelloides, Navicula pelliculosa, Navicula saprophila, Navicula sp., Nephrochloris sp., Nephroselmis sp., Nitschia communis, Nitzschia alexandrine, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia sp., Ochromonas sp., Oocystis parva, Oocystis pusilla, Oocystis sp., Oscillatoria limnetica, Oscillatoria sp., Oscillatoria subbrevis, Parachlorella kessleri, Pascheria acidophila, Pavlova sp., Phaeodactylum tricomutum, Phagus, Phormidium, Platymonas sp., Pleurochrysis camerae, Pleurochrysis dentate, Pleurochrysis sp., Prototheca wickerhamii, Prototheca stagnora, Prototheca portoricensis, Prototheca moriformis, Prototheca zopfii, Pseudochlorella aquatica, Pyramimonas sp., Pyrobotrys, Rhodococcus opacus, Sarcinoid chrysophyte, Scenedesmus armatus, Schizochytrium, Spirogyra, Spirulina platensis, Stichococcus sp., Synechococcus sp., Synechocystisf, Tagetes erecta, Tagetes patula, Tetraedron, Tetraselmis sp., Tetraselmis suecica, Thalassiosira weissflogii, and Viridiella fridericiana.

The microalgae useful for the production of rOPN can be grown on land, for example, in ponds, aqueducts, or in closed or partially closed bioreactor systems. The algae can also be grown directly in water, for example, in an ocean, sea, lake, river, reservoir, etc. The algae may be grown in culture systems of different volumes. In one embodiment, the algae can be grown, for example, in small scale laboratory systems. Small scale laboratory systems refer to cultures in volumes of less than about 6 liters. In an embodiment, the small scale laboratory culture may be 1 liter, 2 liters, 3 liters, 4 liters, or 5 liters. In another embodiment, the small scale laboratory culture may be less than one liter. In yet another embodiment, the small scale laboratory culture may be 100 milliliters or less. In one embodiment the culture may be 10 milliliter or less. In another embodiment the culture may be 5 milliliters or less. In yet another embodiment, the culture may be 1 milliliter or less.

Alternatively, the culture systems may be large scale cultures, where large scale cultures refers to growth of cultures in volumes of greater than about 6 liters, or greater than about 10 liters, or greater than about 20 liters. Large scale growth can also be growth of cultures in volumes of 50 liters or more, 100 liters or more, or 200 liters or more. Large scale growth can be growth of cultures in, for example, ponds, containers, vessels, or other areas, where the pond, container, vessel, or area that contains the culture is for example, at least 5 square meters, at least 10 square meters, at least 200 square meters, at least 500 square meters, at least 1,500 square meters, at least 2,500 square meters, in area, or greater.

The present disclosure further provides for production of rOPN in very large scale culture systems. A very large scale liquid culture system may be from 10,000 to 20,000 liters. In an embodiment, the very large scale culture system may be from 10,000 to 40,000 liters or from 10,000 to 80,000 liters. In another embodiment, the very large scale culture system may be from 10,000 to 100,000 liters or from 10,000 to 150,000 liters. In yet another embodiment, the culture system may be from 10,000 to 200,000 liters or from 10,000 to 250,000 liters. The present disclosure also includes culture systems from 10,000 to 500,000 liters or from 10,000 to 600,000 liters. The present disclosure further provides for culture systems from 10,000 to 1,000,000 liters.

In an aspect of the present disclosure, the culture system may be a pond, either natural or artificial. In one embodiment, the artificial pond may be a raceway pond. In a raceway pond, the algae, water, and nutrients circulate around a "racetrack." Means of motivation, such as paddlewheels, provide constant motion to the liquid in the racetrack, allowing for the organism to be circulated back to the surface of the liquid at a chosen frequency. Paddlewheels also provide a source of agitation and oxygenate the system. $CO_2$ may be added to a culture system as a feedstock for photosynthesis through a $CO_2$ injection system. These raceway ponds can be enclosed, for example, in a building or a greenhouse, or can be located outdoors. In an embodiment, an outdoor raceway culture system may be enclosed with a cover, or exposed.

Alternatively, microalgae producing rOPN can be grown in closed structures such as bioreactors, where the environment is under stricter control than in open systems or semi-closed systems. A photobioreactor is a bioreactor which incorporates some type of light source to provide photonic energy input into the reactor. The term bioreactor can refer to a system closed to the environment and having no direct exchange of gases and contaminants with the environment. A bioreactor can be described as an enclosed, and in the case of a photobioreactor illuminated, culture vessel designed for controlled biomass production of liquid cell suspension cultures. Examples of bioreactors include, for example, glass containers, stainless steel containers, plastic tubes, tanks, plastic sleeves, and bags. In the case of photobioreactors, examples of light sources that can be used include, for example, fluorescent bulbs, LEDs, and natural sunlight. Because these systems are closed everything that the organism needs to grow (for example, carbon dioxide, nutrients, water, and light) must be introduced into the bioreactor.

Bioreactors, despite the costs to set up and maintain them, have several advantages over open systems, they can, for example, prevent or minimize contamination, permit axenic organism cultivation of monocultures (a culture consisting of only one species of organism), offer better control over the culture conditions (for example, pH, light, carbon dioxide, and temperature), prevent water evaporation, lower carbon dioxide losses due to out gassing, and permit higher cell concentrations. On the other hand, certain requirements of bioreactors, such as cooling, mixing, control of oxygen accumulation and biofouling, make these systems more expensive to build and operate than open systems or semi-closed systems.

Microalgae producing rOPN can be continually harvested (as is with the majority of the larger volume cultivation systems), or harvested one batch at a time (for example, as with polyethylene bag cultivation). Batch harvesting is set up with, for example, nutrients, an organism (for example, microalgae), and water, and the organism is allowed to grow until the batch is harvested. With continuous harvesting, a portion of the algal mass can be harvested, for example, either continually, daily, or at fixed time intervals.

The algae may be grown under conditions which permit photosynthesis, however, this is not a requirement (e.g., the organism may be grown in the absence of light). Thus, algae used in the practice of the present disclosure may be phototrophic, mixotrophic or heterotrophic. Phototrophic or photoautotrophic algae are algae that use photon capture as a source of energy and can fix inorganic carbon. As such phototrophic algae are capable of using inorganic carbon in the presence of light as a source of metabolic carbon. As used herein heterotrophic algae refers to algae than cannot use photon capture as an energy source, but must instead rely on organic carbon sources. Mixotrophic algae are those algae that are capable of using photon capture and inorganic carbon fixation to support growth, but in the absence of light may use organic carbon as an energy source. Thus mixotrophic algae have the metabolic characteristics of both phototrophic and heterotrophic algae. In some instances, biomass can be obtained from an organism that has been genetically modified. In some instances the algae may be genetically modified in such a way that photosynthetic capability is diminished or destroyed. In growth conditions where a microorganism is not capable of photosynthesis (naturally or due to genetic modification), the organism will be provided with the necessary nutrients to support growth in the absence of photosynthesis. For example, a culture medium in (or on) which an organism is grown, may be supplemented with any required nutrient, including an organic carbon source, nitrogen source, phosphorous source, vitamins, metals, lipids, nucleic acids, micronutrients, and/ or any organism-specific requirement. Organic carbon sources include any source of carbon which the host organism is able to metabolize including, but not limited to, acetate, simple carbohydrates (e.g., glucose, sucrose, lactose), complex carbohydrates (e.g., starch, glycogen), proteins, and lipids. One of skill in the art will recognize that not all organisms will be able to sufficiently metabolize a particular nutrient and that nutrient mixtures may need to be modified from one organism to another in order to provide the appropriate nutrient mix.

In certain instances, it may be desirable to reduce the amount of liquid contained in the culture of microalgae prior to disrupting the algal cells. Separation of the microalgae from the liquid may be accomplished by methods known to one of ordinary skill in the art. In one aspect, the microalgae may be allowed to settle by gravity and the overlying liquid removed. In another aspect, the microalgae may be harvested by centrifugation of the microalgae containing culture. In an aspect, centrifugation of the liquid culture may be performed in batch mode, using a fixed volume centrifuge. In a different aspect, batch harvesting of the microalgae may be accomplished using a continuous flow centrifuge. In another aspect, the microalgae may be harvested continuously from the growing culture by continuous flow centrifugation. In other aspects dewatering may be accomplished by filtration, for example, tangential flow filtration. In other aspects, dewatering may be accomplished by electrophoresis techniques such as electrolytic coagulation and electrolytic flocculation.

In one aspect of the present disclosure, microalgae grown in the liquid system may be separated from the liquid fraction by flocculation. Flocculation may be accomplished by means of chemical flocculation using synthetic or natural flocculants or by autoflocculation. Methods for inducing flocculation include those that can be found in U.S. Pat. No. 8,969,066 and U.S. Patent Publication No. US 2015/ 0284673 (application Ser. No. 14/649,524) each of which is hereby incorporated in its entirety by reference. The flocculate may be separated from the culture liquid by gravity, centrifugation or other physical method known to those of skill in the art. In a particular embodiment the flocculate may be separated from the culture liquid by dissolved air flotation (DAF).

The microalgae used in the methods of the present disclosure have been genetically modified to produce osteopontin. As algae do not naturally produce osteopontin, for the purposes of this disclosure all osteopontins produced by microalgae are considered to be recombinant osteopontins. The recombinant osteopontins purified using the methods disclosed herein can be encoded by nucleotide sequences obtained from a mammalian species that naturally produces osteopontin. In certain embodiments, the rOPN produced by the algae is a human OPN, a bovine OPN, a caprine OPN, an ovine OPN or a camelid OPN.

The nucleotide sequence encoding the rOPN can be the naturally occurring or wild-type sequence, or can be a modified sequence. Types of modifications include the deletion of at least one nucleic acid, the addition of at least one nucleic acid, or the replacement of at least one nucleic acid. One skilled in the art will know how to make modifications to the nucleotide sequence.

One particular type of modification that can be made to a nucleotide sequence is codon optimization. As is known in the art, one or more codons of an encoding polynucleotide can be "biased" or "optimized" to reflect the codon usage of the host organism. For example, one or more codons of an encoding polynucleotide can be "biased" or "optimized" to reflect chloroplast codon usage or nuclear codon usage. Most amino acids are encoded by two or more different (degenerate) codons, and it is well recognized that various organisms utilize certain codons in preference to others. "Biased" or codon "optimized" can be used interchangeably throughout the specification. Codon bias can be variously skewed in different organisms, including, for example, in algae as compared to humans. Generally, the codon bias selected reflects codon usage of the organism (or organelle therein) which is being transformed with the nucleic acid. A polynucleotide that is biased for a particular codon usage can be synthesized de novo, or can be genetically modified using routine recombinant DNA techniques, for example, by a site directed mutagenesis method, to change one or more codons such that they are biased for chloroplast codon usage. Such preferential codon usage, which is utilized in chloroplasts, is referred to herein as "chloroplast codon usage." Examples of chloroplast and nuclear codon usage for *C. reinhardtii* can be found in the art, for example in U.S. Patent Application Publication No.: 2004/0014174 and International Patent Publication No. WO 2011/063,284, incorporated herein by reference.

Expression of an OPN protein in algae is achieved by the use of an expression vector. An expression vector is a vector designed so that a coding sequence inserted at a particular site will be transcribed and translated into a protein. The expression vector, or a linearized portion thereof, can comprise one or more exogenous nucleotide sequences encoding an OPN of interest. In some instances, a sequence encoding a rOPN is flanked by two sequences that have homology to sequences contained in the microalgae to be transformed.

Homologous sequences are, for example, those that have at least 50%, at least 60%, at least 70%, at least 80%, at least 90%, at least 95%, at least 98%, or at least 99% sequence identity to a reference nucleotide sequence, for example, the nucleotide sequence that is found at the location in the host cell where the sequence encoding the rOPN is to be inserted. Homologous sequences enable recombination of the exogenous sequence into the nuclear or plastid genome of the host algae to be transformed.

In some embodiments, the expression vector comprises a polynucleotide operably linked to one or more control elements, such as a promoter and/or a transcription terminator. A nucleic acid sequence is operably linked when it is placed into a functional relationship with another nucleic acid sequence. For example, DNA for a presequence or secretory leader is operatively linked to DNA for a polypeptide if it is expressed as a preprotein that participates in the secretion of the polypeptide; a promoter is operably linked to a coding sequence if it affects the transcription of the sequence; or a ribosome binding site is operably linked to a coding sequence if it is positioned so as to facilitate translation. Generally, operably linked sequences are contiguous and, in the case of a secretory leader, contiguous and in reading phase. Linking is achieved by ligation at restriction enzyme sites. If suitable restriction sites are not available, then synthetic oligonucleotide adapters or linkers can be used as is known to those skilled in the art. Sambrook et al., *Molecular Cloning, A Laboratory Manual*, $2^{nd}$ Ed., Cold Spring Harbor Press, (1989) and Ausubel et al., *Short Protocols in Molecular Biology*, $2^{nd}$ Ed., John Wiley & Sons (1992).

A regulatory or control element, as the term is used herein, broadly refers to a nucleotide sequence that regulates the transcription or translation of a polynucleotide or the localization of a polypeptide to which it is operatively linked. Examples include, but are not limited to, an RBS, a promoter, enhancer, transcription terminator, a hairpin structure, an RNAase stability element, an initiation (start) codon, a splicing signal for intron excision and maintenance of a correct reading frame, a STOP codon, an amber or ochre codon, and an IRES. A regulatory element can include a promoter and transcriptional and translational stop signals. Elements may be provided with linkers for the purpose of introducing specific restriction sites facilitating ligation of the control sequences with the coding region of a nucleotide sequence encoding a rOPN. Additionally, a sequence comprising a cell compartmentalization signal (i.e., a sequence that targets a polypeptide to the cytosol, nucleus, chloroplast membrane or cell membrane) can be attached to the polynucleotide encoding a rOPN. Such signals are well known in the art and have been widely reported.

In an expression vector, a nucleotide sequence of interest is operably linked to a promoter recognized by the host cell to direct mRNA synthesis. Promoters are untranslated sequences located generally 100 to 1000 base pairs (bp) upstream from the start codon of a structural gene that regulate the transcription and translation of nucleic acid sequences under their control. The promoter can be a constitutive promoter or an inducible promoter. Inducible promoters are promoters that initiate increased levels of transcription from DNA under their control in response to some change in the environment, e.g. the presence or absence of a nutrient or a change in temperature. Constitutive promoters, in contrast, maintain a relatively constant level of transcription.

Many promoters are active in algae, including promoters that are endogenous to the algae being transformed, as well as promoters that are not endogenous to the algae being transformed (i.e., promoters from other algae, promoters from higher plants, and promoters from plant viruses or algae viruses). Exogenous and/or endogenous promoters that are active in algae, and antibiotic resistance genes functional in algae include, but are not limited to, those described in e.g., *Curr. Microbiol.* (1997) 35(6):356-62 (*Chlorella vulgaris*); *Marine Biotechnol.* (NY). (2002) 4(I): 63-73 (*Chlorella ellipsoidea*); *Mol. Gen. Genet.* (1996) 252(5):572-9 (*Phaeodactylum tricornutum*); *Plant Mol. Biol.* (1996) 31(1):1-12 (*Volvox carteri*); *Proc. Natl. Acad. Sci. USA.* (1994) 91(24): 11562-6 (*Volvox carteri*); Falciatore A, Casotti R, Leblanc C, Abrescia C, Bowler C, PMID: 10383998, (1999) 1(3):239-251 (Laboratory of Molecular Plant Biology, Stazione Zoologica, Villa Comunale, 1-80121 Naples, Italy) (*Phaeodactylum tricornutum* and *Thalassiosira weissflogii*); *Plant Physiol.* (2002) 129(1):7-12. (*Porphyridium* sp.); *Proc. Natl. Acad. Sci. USA*, (2003) 100(2):438-42. (*Chlamydomonas reinhardtii*); *Proc. Natl. Acad. Sci. USA.* (1990) 87(3): 1228-32. (*Chlamydomonas reinhardtii*); *Nucleic Acids Res.* (1992) 20(12):2959-65; *Marine Biotechnol.* (NY). (2002) 4(1):63-73 (*Chlorella*); *Biochem. Mol. Biol. Int.* (1995) 36(5): 1025-35 (*Chlamydomonas reinhardtii*); *J. Microbiol.* (2005) 43(4):361-5 (*Dunaliella*); *Marine Biotechnol.* (NY) (1999) 1(3):239-251. (*Thalassiosira* and *Phaedactylum*); *Appl. Microbiol. Biotechnol.* (2002) 58(2): 123-37 (various species); *Mol. Genet. Genomics* (2004) 271(1):50-9 (*Thermo synechococcus elongates*); *J. Bacteriol.* (2000), 182, 211-215; *FEMS Microbiol. Lett.* (2003) 221(2):155-9; *Plant Physiol.* (1994) 105(2):635-41; *Plant Mol. Biol.* (1995) 29(5):897-907 (*Synechococcus* PCC 7942); *Marine Pollut. Bull.* (2002) 45(1-12): 163-7 (*Anabaena* PCC 7120); *Proc. Natl. Acad. Sci. USA.* (1984) 81(5): 1561-5 (*Anabaena* (various strains)); *Proc. Natl. Acad. Sci. USA.* (2001) 98(7):4243-8 (*Synechocystis*); *Mol. Gen. Genet.* (1989) 216(1): 175-7 (various species); *Mol. Microbiol.* (2002) 44(6):1517-31; *Plasmid* (1993) 30(2):90-105 (*Fremyella diplosiphon*); *Gene* (1993) 124: 75-81 (*Chlamydomonas reinhardtii*); *Current Micro.* (1991) 22: 15-20; *Current Genet.* (1991) 19: 317-322 (*Chlorella*). Additional promoters can be found in Table 1 of U.S. Pat. No. 6,027,900.

A polynucleotide encoding a rOPN can be introduced into an alga cell using any method known in the art. A polynucleotide can be introduced into the cell by a variety of methods, which are well known in the art and selected, in part, based on the particular host cell. For example, the polynucleotide can be introduced into a cell using a direct gene transfer method such as electroporation or microprojectile mediated (biolistic) transformation using a particle gun, or the "glass bead method" or liposome-mediated transformation.

Microprojectile mediated transformation utilizes microprojectiles such as gold or tungsten, that are coated with the desired polynucleotide by precipitation with calcium chloride, spermidine or polyethylene glycol. The microprojectile particles are accelerated at high speed into a cell using a device such as the BIOLISTIC PD-1000 particle gun (Bio- Rad; Hercules Calif.). Methods for the transformation using biolistic methods are well known in the art (for example, as described in Christou, *Trends in Plant Science* (1996) 1:423-431). Exemplary methods for the transformation of algae can be found in International Patent Application Publication Nos. WO 2011/034,863 and WO 2011/063,284 as well as *Biosci. Biotechnol. Biochem*. (2014) 78:812-7; *J. Biosci. Bioeng*. (2013) 115:691-4; *Proc. Natl. Acad. Sci. USA* (2011) 108:21265-9; and *Plant Physiol*. (2002) 129:7-12; *Adv. Expl. Med. Biol*. (2007) 616:1-9; *Molec. Biotechnol.* (2005) 30:185-91; *Science* (1988) 240:1534-38; *Folia Microbiol*. (2000) 45:496-504; *Plant Physiol*. (2002) 129: 7-12; *Molec. Gen. Genetics* (2000) 263:404-10; *J. Biosci. Bioeng*. (1999) 87:307-14; *Proc. Natl. Acad. Sci. USA* (1990) 87:2087-90; *Plant Cell* (1989) 1:123-32; *Plant Biotechnol. J*. (2007) 5:402-12; and *J. Biotechnol*. (2013) 163:61-8.

The rOPN may be expressed in the nucleus or in a plastid such as the chloroplast. When nuclear transformation is utilized, the protein can be modified for plastid targeting by employing nuclear transformation constructs wherein DNA sequences coding a rOPN are fused to any of the available transit peptide sequences capable of facilitating transport of the encoded rOPNs into plant plastids, and driving expression by employing an appropriate promoter. Targeting of the rOPN can be achieved by fusing DNA encoding plastid, e.g., chloroplast, transit peptide sequences to the 5' end of the DNA encoding the rOPN. The sequences that encode a transit peptide region can be obtained, for example, from plant nuclear-encoded plastid proteins, such as the small subunit (SSU) of ribulose bisphosphate carboxylase, EPSP synthase, plant fatty acid biosynthesis related genes including fatty acyl-ACP thioesterases, acyl carrier protein (ACP), stearoyl-ACP desaturase, β-ketoacyl-ACP synthase and acyl-ACP thioesterase, or LHCPII genes, etc. Plastid transit peptide sequences can also be obtained from nucleic acid sequences encoding carotenoid biosynthetic enzymes, such as GGPP synthase, phytoene synthase, and phytoene desaturase. Other transit peptide sequences are disclosed in *Plant Mol. Biol. Rep*. (1991) 9: 104; *J. Biol. Chem*. 1989 264: 17544; *Plant Physiol*. (1987) 84: 965; *Biochem. Biophys. Res. Commun*. (1993) 196: 1414; and *Science* (1986) 233: 478. Another transit peptide sequence is that of the intact ACCase from *Chlamydomonas* (Genbank ED096563, amino acids 1-33). The encoding sequence for a transit peptide effective in transport to plastids can include all or a portion of the encoding sequence for a particular transit peptide, and may also contain portions of the mature protein encoding sequence associated with a particular transit peptide. Numerous examples of transit peptides that can be used to deliver target proteins into plastids exist, and the particular transit peptide encoding sequences useful in the present disclosure are not critical as long as delivery into a plastid is obtained. Proteolytic processing within the plastid then produces the mature rOPN.

Unless the transgenic algae secretes the rOPN into the surrounding medium, it will be necessary to disrupt the cell structure of the algae in order to release the rOPN. If the rOPN is produced or stored in a plastid, it may be necessary to disrupt the plastid membrane as well. Various methods are known in the art for the disruption of cell and plastid membranes. One of ordinary skill in the art can readily select a suitable method or combination of methods to meet their particular circumstances without the need for undue experimentation.

One routinely used method called bead beating involves mechanical disruption by the use of very small beads typically made of glass, ceramic or stainless steel. In this method the cells and beads are mixed together and the mixture subjected to a high degree of agitation by stirring or shaking. As the cells and bead collide the cells are broken open releasing their intracellular contents. Use of this method has the advantage that sheer forces are very low. Cell lysis can also be achieved by the application of high shear forces. One method of applying such forces is by use of a French press. A French press uses high pressure to force cells through a narrow orifice. The resulting high shear pressures result in rupture of the cell membrane. French presses typically apply force by pneumatic or hydraulic means. A related method is the use of homogenizers such as a dounce homogenizer. In this method shear forces are created by forcing the sample between sides of a tube and a pestle which may be rotating at high speed. Still another method to disrupt cells that may be utilized is the microfluidizer method. In a microfluidizer cells are forced through microchannels of fixed geometry by means of an intensifier pump which creates high shear forces resulting in high rates of cell membrane disruption.

Disruption using sonication depends on the generation of shock waves. Shock waves are created by a probe that rapidly expands and contracts a high frequency in response to oscillating current. When the probe contracts, negative pressure causes the liquid to flow up the probe while the expansion of the probe pushes the liquid. At a rate of 20 kHz, the liquid turns into a zone of microscopic shockwaves. The shock waves created are quite powerful and disrupt cell membranes with high efficiency.

Another method by which cells can be disrupted is nitrogen decompression. In this method large quantities of nitrogen are dissolved in the cell under high pressure. Next the pressure is rapidly released. The decompression results in the nitrogen rapidly coming out of solution and the resulting bubbles rupture the cell membranes.

In another embodiment, cell lysis is accomplished by the use of acid treatment. In this embodiment an acid is added to the algae at a concentration of between about 40 nM and 160 nM. Acid treatment is typically performed at a temperature that allows cell disruption to occur rapidly without damaging the OPN. In certain embodiment the algal cells are disrupted by exposing the cells to a pH of between about pH 3.8 and about 5.5 or between about pH 4.3 and about pH 6.0. In one embodiment, algal cells are disrupted by exposure to a pH of about 5.0. The optimal combination of temperatures and acid concentrations will vary depending on the species of algae used. Determining the optimal conditions can be routinely accomplished by one of ordinary skill in the art.

As will be apparent to one of skill in the art, cell to be disrupted will typically be in a liquid medium. In some embodiments, the liquid medium will contain a buffer to maintain the pH within desired limits. Examples of suitable buffers that may be utilized during cell disruption include, but are not limited to, acetate buffers, phosphate buffers, citrate buffers and tris buffers.

The above examples of method of cell disruption are for illustrative purposes and not intended to be limiting. One of skill in the art will be able to envision alternative methodologies. It also will be readily apparent to one of skill in the art that the above methods of cell disruption can be used individually or in any combination.

As a result of cell disruption, soluble and insoluble cellular fractions are produced with the rOPN contained in the soluble fraction. The soluble and insoluble fractions are then separated using any method or combination of methods known in the art. For example, the insoluble and soluble fractions may be separated by sedimentation, filtration, centrifugation or any combination of these techniques. For sedimentation, the preparation containing the soluble and insoluble fractions is allowed to stand, without agitation, for a time sufficient for the insoluble fraction to settle to the bottom.

If filtration is utilized, any means of filtration known in the art may be utilized, alone or in combination with other techniques. As will be apparent to one of skill in the art, the exact method of filtration chosen will depend on a number of factors, including, but not limited to, the volume of material to be filtered. In one embodiment filtration is accomplished by gravity flow of the material through a semipermeable membrane where the rOPN is found in the filtrate (permeate) and the cellular membrane fraction in the retentate. In some embodiments the rate of filtration is enhanced by the application of a vacuum or positive pressure. The configuration of the semipermeable membrane may be a substantially planar surface or tubular. In certain embodiments tangential flow filtration is used As will be apparent to one of skill in the art, it is important to select the appropriate pore size of the semipermeable membrane. The pore size should be selected so that rOPN is allowed to pass through the membrane into the filtrate, while larger molecules and insoluble materials are held in the retentate. In various embodiments, the pore size of the semipermeable membrane is such that materials having a molecular weight of greater than 50 kDa, greater than 75 kDa, greater than 100 kDA, greater than 250 kDa, greater than 500 kDa, greater than 750 kDa or greater than 1000 kDa are retained by the semipermeable membrane. In one embodiment, ultrafiltration is not utilized in the practice of the disclosed methods. For the purposes of this disclosure, ultrafiltration is defined as means of filtration utilizing semipermeable membranes in which materials having a molecular weight of less than 50 kDa are retained by the membrane.

In another embodiment, the soluble and insoluble cellular fractions are separated by centrifugation. As with filtration, the exact means of centrifugation utilized will vary, among other factors, with the volume of material to be processed. In some embodiments a table top centrifuge is used while in other embodiments, a floor model centrifuge can be used. In the case of either a table top or floor model centrifuge a fixed angle or swinging bucket rotor may be utilized. In some embodiments the soluble and insoluble fractions may be separated by continuous centrifugation. Examples of means for continuous centrifugation include stack-disc and decanter centrifuges. In some embodiments the material is centrifuged at approximately 10,000×g.

In some embodiments the separation of the soluble and insoluble cellular fractions is accomplished at ambient temperature. In other embodiments, the separation of the soluble and insoluble cellular fractions is carried out at a temperature below ambient temperature. In certain embodiment the separation is carried out at between about 0° C. and 20° C., between about 0° C. and 15° C., 0° C. and 10° C., or 0° C. and 5° C.

Following separation from the insoluble cellular fraction, the rOPN is precipitated from the soluble cellular fraction by increasing the pH of the soluble fraction in the presence of a soluble calcium salt. The pH of the soluble cellular fraction is increased by the addition of a base. Bases that may be utilized in the practice of the claimed methods include hydroxides of alkali metals and alkali earth metals such as sodium hydroxide, potassium hydroxide and magnesium hydroxide. In one embodiment, a base is added to increase the pH to between about pH 5.0 and pH 9.0. In another embodiment, the pH is increase to between about pH 7.5 and pH 8.5. In one particular embodiment, the pH of the soluble fraction is increased to a pH of about 8.0.

The amount of the soluble calcium salt that is used to precipitate the rOPN will vary with the particular salt used and the amount of rOPN present. One of skill in the art can readily determine the concentration of calcium salt required using routine methods, but the concentration of calcium salts will generally be between about 100 mM and about 250 mM. Non-limiting examples of calcium salts that may be used in the methods disclosed herein include calcium chloride, calcium citrate, calcium sulphate, calcium fluoride, calcium phosphate, calcium carbonate or any combination thereof.

The precipitated rOPN is then separated from the fluid supernatant. Any means known in the art to separate the precipitate from the supernatant can be utilized, including, but not limited to, sedimentation, centrifugation and filtration. Sedimentation and centrifugation can be carried out essentially as described herein with the exception that in this case the precipitate or pellet in the case of sedimentation and centrifugation is retained and the liquid portion (supernatant) is discarded. In the case of filtration the retentate rather than the filtrate is saved. In addition, in this instance the pore size of the semipermeable membrane is selected so that the precipitated rOPN is held in the retentate.

The rOPN in the retentate is then solubilized in a solution having a pH between about pH 4.3 and about pH 5.0. In certain embodiments the pH of the solution is between about pH 4.7 and about pH 5.0, while in a particular embodiment the pH of the solution is about 5.0. The solution used to solubilize the rOPN may optionally contain a buffer. Any buffer with a useful range between about pH 4 and 6 can be used. Non-limiting examples of suitable buffers include sodium acetate buffer, sodium citrate buffer, phosphate citrate buffer, sodium phosphate buffer and potassium phosphate buffer.

The decreased pH of the solubilization solution results in precipitation of the calcium. The precipitated calcium is removed from the solubilization solution by any of the means known in the art, including, but not limited to, sedimentation, centrifugation and filtration as described herein.

Following removal of the precipitated calcium, the solubilization solution containing the rOPN is applied to an anion exchange medium. Ion exchange is a method of separating ionizable molecules based on their total charge. In anion exchange, an ionizable molecule is placed in a medium having a pH greater than its isoelectric point. In this environment, the molecule will have a negative charge and will bind by electrostatic forces to the positively charged anion exchange resin. Because a protein's isoelectric point is based on its primary amino acid sequence, one of skill in the art can readily estimate the isoelectric point of a protein and thus determine the appropriate conditions to ensure a net negative charge for use in anion exchange. For example, milk OPN typically has an isoelectric point of less than 4.5, so that a pH of greater than 4.5 is appropriate. One of skill in the art will also appreciate that OPN from different species or different tissues within a species may have different isoelectric points. In general, purification of OPN by anion exchange chromatography is conducted at a pH between about 4.0 and 6.0.

Typically, ion exchange is conducted by allowing the resin to equilibrate with the pH of the medium to be used. Following equilibration, the sample containing the protein to be purified is applied to the resin and the protein allowed to bind to the resin. The resin is then washed to remove unbound proteins and the protein of interest is then eluted by altering the pH of the medium to neutralize the charge of the protein. Alternatively a charged salt ion gradient is used where the salt ions compete with the protein for resin binding sites. Elution of the protein can be either by means of a linear gradient elution or a step isocratic elution. A linear gradient elution is typically used with salt ion elutions and a step isocratic elution with pH elutions. In one embodiment, the rOPN is eluted from the anion exchange resin by application of a 200 mM to 400 mM linear salt gradient. In a particular embodiment, the salt used in the gradient is sodium chloride.

Ion exchange is typically carried out by allowing medium to flow over the resin which is contained in a column, although other configurations can be used. Columns suitable in the practice of the methods disclosed herein include, but are not limited to, gravity columns, spin columns, high pressure columns and medium pressure columns. As the gradient is applied to the resin, fractions of the eluted material are collected and tested for the presence of the rOPN. In this manner the rOPN is separated from the unwanted proteins.

The anion exchange resin used can be a strong or weak anion exchange resin. A non-limiting example of a strong anion exchange resin is a Q resin, while a non-limiting example of a weak ion exchange resin is a DEAE anion exchange resin. Other suitable ion exchange resins will be apparent to one of skill in the art.

Application of the methods described herein results in the production of a substantially pure preparation of rOPN from an algal culture. Substantially pure, in the context of this disclosure, means that the rOPN is free from other contaminating proteins, nucleic acids, and other biologicals derived from the original source algae. Purity may be assayed by standard methods, and will ordinarily be at least about 20% pure, at least about 40% pure, at least about 50% pure, at least about 60% pure, at least about 70% pure, at least about 75% pure, at least about 80% pure, at least about 85% pure, at least about 90% pure, at least about 95% pure, at least about 98% pure, or at least about 99% pure. The analysis may be weight or molar percentages, evaluated, for example by, by gel staining, spectrophotometry, or terminus labeling.

EXAMPLES

The following examples are intended to provide illustrations of the application of the presently claimed invention. The following examples are not intended to completely define or otherwise limit the scope of the claimed invention.

Example 1. Expression Vector Construction

All DNA manipulations were performed by standard DNA methods. The bovine osteopontin gene and FAM20C genes were synthesized de novo using *C. reinhardtii* chloroplast codon bias from //www.kazusa.or.jp/codon/cgi-binishowcodon.cgi?species=3055.chloroplast. The bovine osteopontin gene was ligated downstream of a sequence coding for a 1× flag peptide (DYDDDDKS) (SEQ ID NO: 1). The synthesized osteopontin gene product has a codon adaption index=0.972 and Nc=24.6. This gene product was placed downstream of the 16 promoter and 5'UTRs corresponding to 65 different genes expressed in *C. reinhardtii* chloroplasts and upstream of the rbcL 3'UTR. A kanamycin resistance gene (aphaVI) was used to select algae that were transformed with the recombinant genes. The expression of the aphaVI gene was driven by the psbD promoter and 5'-UTR and placed upstream of a second rbcL 3-UTR. Flanking regions for the psbH locus were placed on either end of the transformation construct to allow for integration of the transgenic bovine osteopontin gene upstream of the the psbH locus (FIG. 1A) (ref). The two rbcL 3'-UTRs allow for the removal of the aphaVI selection marker once the transgenic strains are removed from selection.

Figure 1:
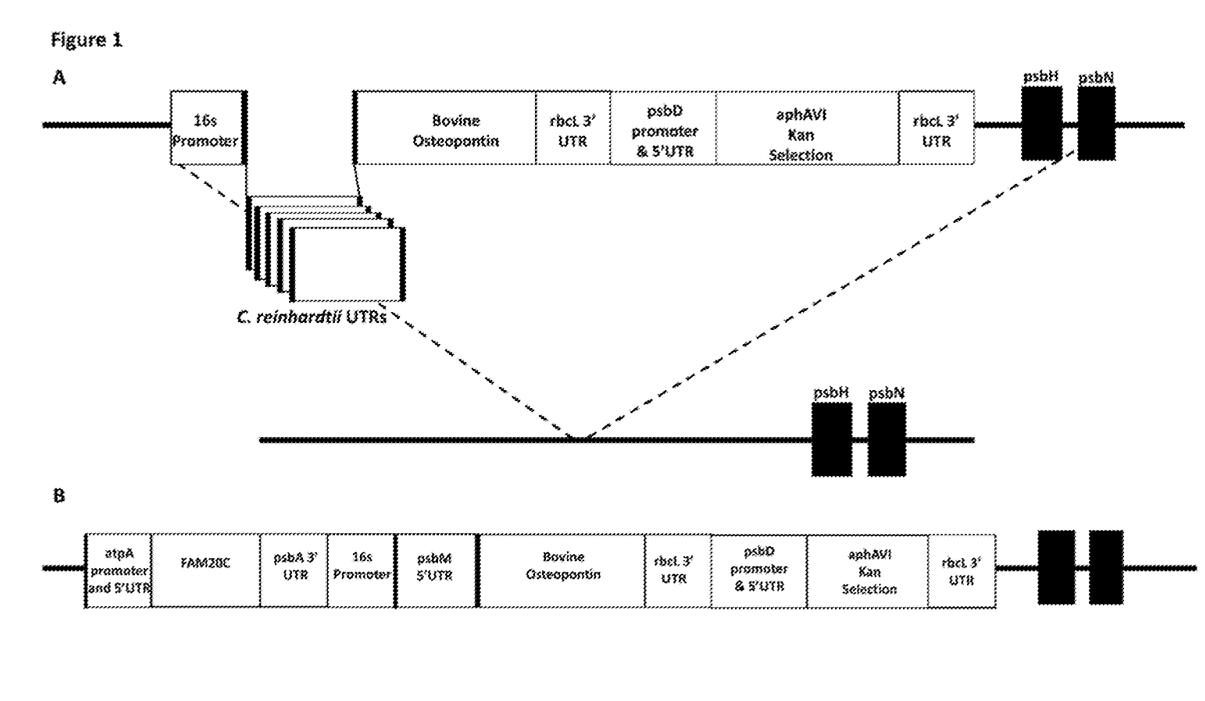
FIG. 1 shows vectors used to express rOPN in algae

To co-express the golgi kinase, FAM20C, with bovine osteopontin an expression cassette was engineered upstream of the 16s promoter used to drive transcription of bovine osteopontin. This expression cassette contained the promoter and 5'-UTR of the atpA gene and a 3'-UTR of the psbA gene (FIG. 1). The FAM20C gene had a codon adaption index=0.954 and a NC=24.2 (FIG. 1B).

Example 2. Analysis of Gene Integration into the Chloroplast Genome

Transgenic strains obtained after particle bombardment were screened for the presence of the transgenic bovine osteopontin gene. PCR analysis was used to identify several transgenic lines that contain the bovine osteopontin gene. Forward Primer (5'-TACAGAATCAGCTAAT-GATGGTCGTGGTG-3') (SEQ ID NO: 2) and Reverse primer (5'-GCTGAACGAATTACGTCGCCACCTT-CACG-3') (SEQ ID NO: 3) were used in a PCR to detect the presence of a 500-bp product that coincides with strains of *C. reinhardtii* that are transformed with the bovine osteopontin gene. Chloroplasts of *C. reinhardtii* contain up to 80 copies of their genome and to identify transgenic strains where the bovine osteopontin gene has be stably integrated, a homoplasmic screen was performed to ensure that the transgene could not be removed by the host cell. A PCR screen was employed to determine the level of homoplasmicity of each of the transgenic strains (U.S. Pat. No. 8,268,553). Primers against the sequence coding for the 16sRNA gene Forward: 5'-CCGAACT-GAGGTTGGGTTTA-3'(SEQ ID NO: 4) and Reverse 5'-GGGGGAGCGAATAGGATTAG-3' (SEQ ID NO: 5)) and primers which reside in the locus of the wt (cc1690 mt+) parental strain (Forward 5'-CGTCCACTAAAATTTATT-TACCCGAAGGGG-3' (SEQ ID NO: 6) and Reverse 5'-GT-TAAGGCTAGCTGCTAAGTCTTCTTTTCGC-3' (SEQ ID NO: 7)) were used in conjunction with control primers against the site of integration. Loss of the amplicon from the site of integration implies a stably transformed strain of *C. reinhardtii*. All strains tested were determined to be homplasmic before further analysis was performed.

Figure 2:
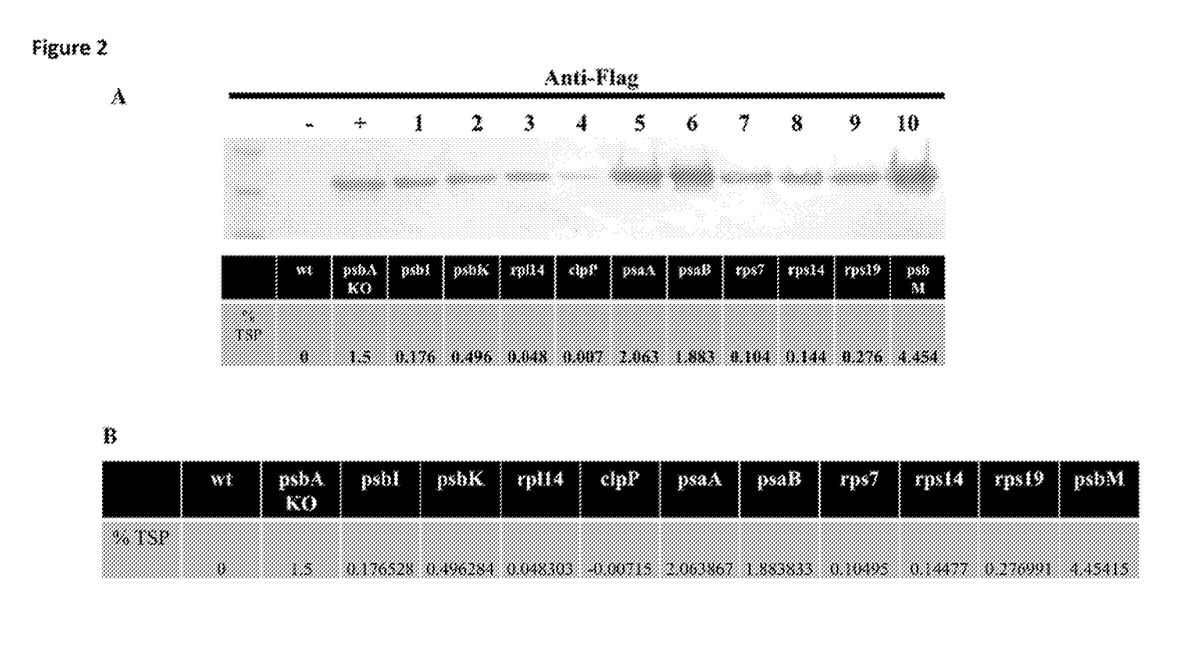
FIG. 2 shows the effect of various promoters on expression of rOPN in algae. % TSP is percent total soluble protein.
Figure 3:
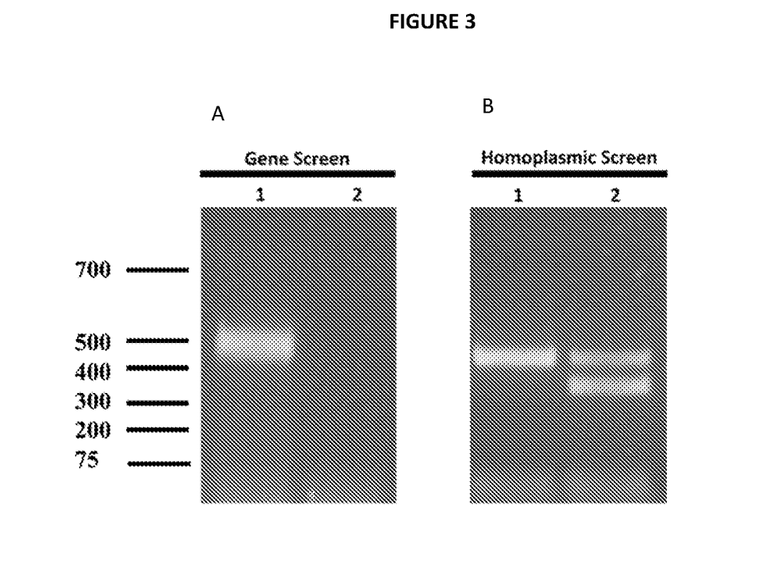

Example 3. Analysis of Recombinant Osteopontin Accumulation in Transgenic Algal Strains To determine if *C. reinhardtii* chloroplasts accumulate bovine osteopontin protein, western blot analysis with an anti-FLAG antibody conjugated with alkaline phosphatase was used (FIG. 2A). Algal lysate from strains that were transformed with the top 10 performing vectors were compared. Ten micrograms of total soluble protein was added to each well and proteins were separated by polyacrylamide gel electrophoresis. Once separated proteins were transferred to a nitrocellulose membrane. The membrane was blocked and an anti-flag antibody used to probe for the presence of osteopontin. To determine which of the generated vectors accumulated the most protein, the top 10 vectors were compared to the previous best expression vector which when transformed into chloroplasts of *C. reinhardtii* to directly replace the psbA gene with the recombinant osteopontin gene (FIG. 2B). To determine the percent expression of bovine osteopontin in transgenic *C. reinhardtii* chloroplasts, an ELISA assay was used. As determined by ELISA, chloroplast can accumulate bovine OPN to ~4.5% of total soluble protein. This is a 3-fold increase in protein expression as a function of total soluble protein.

Example 4. Purification of Bovine Osteopontin from *C. reinhardtii* Chloroplasts To purify bovine osteopontin, 20 L of transgenic *C. reinhardtii* strain expressing the bOPN gene was grown. Cells were harvested and subsequently ruptured using a freeze thaw strategy in 50 mM NaOAc pH5.0). Soluble and insoluble fractions were then separated by centrifugation (10,000×g). The soluble lysate was then adjusted to pH 8.0 and calcium chloride added to a final concentration of 250 mM to allow the bovine osteopontin to precipitate from solution. The precipitated pellet was then separated from the soluble fraction by centrifugation at 10,000×g. Following the precipitation of osteopontin, the pellet was re-suspended in NaOAc 50 mM, pH5.0 to allow bovine osteopontin to solubilize. The sample was then centrifuged at 10,000×g to remove the calcium chloride. The solubilized osteopontin was then applied to the weak anion exchange column (DEAE-sepharose). Osteopontin was then eluted using a concentration of 400 mM NaCl.

The degree of purification was determined using an ELISA assay. Equal amounts (500 ng) of total protein from each of the soluble lysate, calcium chloride pellet, resuspended calcium chloride pellet, and anion exchange chromatography were assayed for bOPN. Total protein was determined using the Bio Rad DC protein assay (Bio Rad Laboratories, Hercules, Calif.). The amount of bOPN present as a percent of total protein is shown in Table 1.

TABLE 1

| Purification Step | Soluble lysate | CaCl$_2$ Pellet | Solubilized Pellet | Anion Exchange |
|---|---|---|---|---|
| Total Protein (ng) | 500 | 500 | 500 | 500 |
| bOPN (ng) | 17.36 | 97.36 | 143.95 | 407.74 |
| Percent purity | 3.5% | 19.5% | 28.8% | 81.6% |

It is to be understood that the claimed invention has been described in detail by way of illustration and example in order to acquaint others skilled in the art with the claimed invention, its principles, and its practical application. Particular formulations and processes of the claimed invention are not limited to the descriptions of the specific embodiments presented, but rather the descriptions and examples should be viewed in terms of the claims that follow and their equivalents. While some of the examples and descriptions above include some conclusions about the way the claimed invention may function, the inventors do not intend to be bound by those conclusions and functions, but put them forth only as possible explanations.

It is to be further understood that the specific embodiments set forth above are not intended as being exhaustive or limiting of the claimed invention, and that many alternatives, modifications, and variations will be apparent to those of ordinary skill in the art in light of the foregoing examples and detailed description. Accordingly, the claimed invention is intended to embrace all such alternatives, modifications, and variations that fall within the scope of the following claims.

The invention claimed is:

1. A method for obtaining a purified recombinant osteopontin comprising:
   obtaining a transgenic microalgae expressing a recombinant osteopontin (rOPN);
   disrupting a cell structure of the transgenic microalgae in a liquid environment having a first pH of between 4.3 and 8.5 to produce soluble and insoluble cellular fractions, wherein the rOPN is in the soluble fraction;
   separating the soluble and insoluble fractions;
   increasing the pH of the soluble fraction to a second pH of between 5.0 and 9.0 in the presence of a soluble calcium salt to form a precipitate containing the rOPN and a supernatant;
   separating the precipitate from the supernatant;
   solubilizing the rOPN in a liquid having a third pH of between 4.3 and 5.0;
   removing the calcium salt from the solubilized rOPN;
   applying the solubilized rOPN to an anion exchange medium, wherein the rOPN binds to the anion exchange medium;
   eluting the bound rOPN from the anion exchange medium; and
   collecting the rOPN to obtain a purified rOPN.

2. The method of claim 1, wherein the rOPN is expressed in a plastid.

3. The method of claim 2, wherein the plastid is a chloroplast.

4. The method of claim 1, wherein the rOPN is a human OPN, a bovine OPN, a caprine OPN, an ovine OPN or a camelid OPN.

5. The method of claim 1 wherein the microalgae cell structure is disrupted by freezing and thawing, bead beating, acid hydrolysis, homogenization, microfluidization, French press, sonication, enzymatic treatment or nitrogen decompression.

6. The method of claim 1, wherein the first pH is between 4.3 and 6.0.

7. The method of claim 6, wherein the first pH is about 5.0.

8. The method of claim 1, wherein the second pH is between 6.0 and 8.5.

9. The method of claim 1, wherein the soluble calcium salt is calcium chloride, calcium citrate, calcium sulphate, calcium fluoride, calcium phosphate or calcium carbonate.

10. The method of claim 1, wherein the third pH is between 4.5 and 5.0.

11. The method of claim 1, wherein said purified rOPN is at least 50% pure by weight.

12. The method of claim 1, wherein said purified rOPN is at least 90% pure by weight.

13. The method of claim 1, wherein said purified rOPN is at least 95% pure by weight.

14. The method of claim 1, wherein the transgenic microalgae is a *Chlamydomonas* species.

15. The method of claim 14, wherein the transgenic microalgae is *Chlamydomonas reinhardtii*.

16. The method of claim 1, wherein the transgenic microalgae express a recombinant golgi kinase.

17. The method of claim 1, wherein the recombinant rOPN is codon optimized for expression in a chloroplast.

18. The method of claim 1, wherein the first pH is between 4.3 and 6.0 and the second pH is between 6.0 and 8.5.

* * * * *

SEQUENCE LISTING

<160> NUMBER OF SEQ ID NOS: 7

<210> SEQ ID NO 1
<211> LENGTH: 8
<212> TYPE: DNA
<213> ORGANISM: Artificial Sequence
<220> FEATURE:
<223> OTHER INFORMATION: Synthetic Construct

<400> SEQUENCE: 1 dydddkks                                                                 8

<210> SEQ ID NO 2
<211> LENGTH: 29
<212> TYPE: DNA
<213> ORGANISM: Artificial Sequence
<220> FEATURE:
<223> OTHER INFORMATION: Synthetic Construct

<400> SEQUENCE: 2
tacagaatca gctaatgatg gtcgtggtg                                          29

<210> SEQ ID NO 3
<211> LENGTH: 29
<212> TYPE: DNA
<213> ORGANISM: Artificial Sequence
<220> FEATURE:
<223> OTHER INFORMATION: Synthetic Construct

<400> SEQUENCE: 3

```
gctgaacgaa ttacgtcgcc accttcacg                                              29
```

```
<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
ccgaactgag gttgggttta                                                        20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
gggggagcga ataggattag                                                        20

<210> SEQ ID NO 6
<211> LENGTH: 30
<212> TYPE: DNA
<213> ORGANISM: Artificial Sequence
<220> FEATURE:
<223> OTHER INFORMATION: Synthetic Construct

<400> SEQUENCE: 6
cgtccactaa aatttattta cccgaagggg                                             30

<210> SEQ ID NO 7
<211> LENGTH: 31
<212> TYPE: DNA
<213> ORGANISM: Artificial Sequence
<220> FEATURE:
<223> OTHER INFORMATION: Synthetic Construct

<400> SEQUENCE: 7
gttaaggcta gctgctaagt cttcttttcg c                                           31
```

UNITED STATES PATENT AND TRADEMARK OFFICE
CERTIFICATE OF CORRECTION

PATENT NO. : 10,954,280 B2
APPLICATION NO. : 16/349116
DATED : March 23, 2021
INVENTOR(S) : Miller Tran et al.

Page 1 of 1

It is certified that error appears in the above-identified patent and that said Letters Patent is hereby corrected as shown below:

On the Title Page

Item (54) and in the Specification, Column 1, Lines 1-3:
Please update the title from "METHOD OF PURIFICATION OF RECOMBINANT OSTEOPONTIN FROM MICRO ALGAE" and replace it with --METHOD OF PURIFICATION OF RECOMBINANT OSTEOPONTIN FROM MICROALGAE--.

In the Specification

At Column 4, Line 48:
Delete "tennis" and replace it with --tenuis--.

In the Claims

At Column 20, Line 61:
Delete "about".

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*